(12) United States Patent
Landau et al.

(10) Patent No.: US 7,131,961 B2
(45) Date of Patent: Nov. 7, 2006

(54) NEEDLE-FREE INJECTION SYSTEM

(75) Inventors: Sergio Landau, Laguna Niguel, CA (US); Robert B. Hubler, Woodinville, WA (US); John M. Stiggelbout, Sausalito, CA (US)

(73) Assignee: Bioject, Inc., Tualatin, OR (US)

( * ) Notice: Subject to any disclaimer, the term of this patent is extended or adjusted under 35 U.S.C. 154(b) by 328 days.

(21) Appl. No.: 10/740,653

(22) Filed: Dec. 17, 2003

(65) Prior Publication Data

US 2005/0075601 A1   Apr. 7, 2005

Related U.S. Application Data

(60) Provisional application No. 60/508,066, filed on Oct. 1, 2003.

(51) Int. Cl.
*A61M 5/30* (2006.01)
(52) U.S. Cl. .................................... 604/71; 604/68
(58) Field of Classification Search ............ 604/68–71, 604/304–307, 112; 222/325–327; 128/919
See application file for complete search history.

(56) References Cited

U.S. PATENT DOCUMENTS

| | | | |
|---|---|---|---|
| 2,547,099 A | 4/1951 | Smoot | |
| 2,653,603 A * | 9/1953 | Hein, Jr. ................... | 604/71 |
| 2,704,543 A | 3/1955 | Scherer | |
| 2,737,946 A | 3/1956 | Hein, Jr. | |
| 2,764,977 A | 10/1956 | Ferguson | |
| 3,688,765 A | 9/1972 | Gasaway | |
| 3,695,266 A | 10/1972 | Lussier | |
| 3,853,125 A | 12/1974 | Clark et al. | |
| 3,859,996 A | 1/1975 | Mizzy et al. | |
| 3,945,383 A | 3/1976 | Bennett et al. | |
| 4,403,989 A | 9/1983 | Christensen et al. | |
| 4,596,556 A | 6/1986 | Morrow et al. | |
| 4,680,027 A | 7/1987 | Parsons et al. | |
| 4,717,384 A | 1/1988 | Waldeisen | |
| 4,790,824 A | 12/1988 | Morrow et al. | |
| 5,569,189 A | 10/1996 | Parsons | |
| 6,168,587 B1 | 1/2001 | Bellhouse et al. | |
| 6,817,986 B1 * | 11/2004 | Slate et al. ................... | 604/68 |
| 2005/0085767 A1 * | 4/2005 | Menassa ....................... | 604/68 |

FOREIGN PATENT DOCUMENTS

CA          492587         5/1953

* cited by examiner

*Primary Examiner*—Kevin C. Sirmons
*Assistant Examiner*—Catherine N. Witczak
(74) *Attorney, Agent, or Firm*—Kolisch Hartwell, P.C.

(57) ABSTRACT

A needle-free injection device capable of delivering pressurized injections to an injection site. The device may include a barrier dispenser configured to provide a disposable piece of barrier material for each injection, so as to reduce risk of cross-contamination. The device may also include various sensors, a firing disable mechanism, a multiple use and/or disposable fluid path, and/or other mechanisms configured to enhance sterility and prevent contamination.

30 Claims, 6 Drawing Sheets

NEEDLE-FREE INJECTION SYSTEM

CROSS-REFERENCE TO RELATED APPLICATIONS

This application is based upon and claims the benefit under 35 U.S.C. § 119(e) of U.S. provisional patent application: Ser. No. 60/508,066, filed Oct. 1, 2003, which is incorporated herein by reference in its entirety for all purposes.

BACKGROUND

Needle-free injection systems provide an alternative to standard fluid delivery systems, which typically use a needle adapted to penetrate the outer surface of an injection site. Typically, needle-free injection systems are designed to eject the fluid from a fluid chamber with sufficient pressure to allow the fluid to penetrate the target to the desired degree. For example, common applications for needle-free injection systems include delivering intradermal, subcutaneous and intramuscular injections into or through a recipient's skin. For each of these applications, the fluid must be ejected from the system with sufficient pressure to allow the fluid to penetrate the tough exterior dermal layers of the recipient's skin.

There has been increased interest in using needle-free injection systems to deliver injections to large numbers of individuals, i.e. for inoculations, immunizations, etc. When using the same device to deliver inoculations, immunizations or the like, it is desirable for the device to be reloaded and capable of delivering the next injection relatively quickly, i.e. without significant time passing between injections. However, preventing cross-contamination between injection recipients must be a priority. Thus, it is desirable to provide a device that allows a user to move with reasonable speed from one injection recipient to another while maintaining adequate protections against cross-contamination. In addition, it will often be desirable to obtain the above advantages while also keeping waste to a minimum (e.g., by avoiding unnecessary disposal of portions of the injection system).

BRIEF DESCRIPTION OF THE DRAWINGS

FIGS. 6 and 7 are partial-sectional views depicting an exemplary safety mechanism. FIG. 6 depicts the safety mechanism in an unlocked state while FIG. 7 depicts the safety mechanism in a locked state.

DETAILED DESCRIPTION

Figure 1:
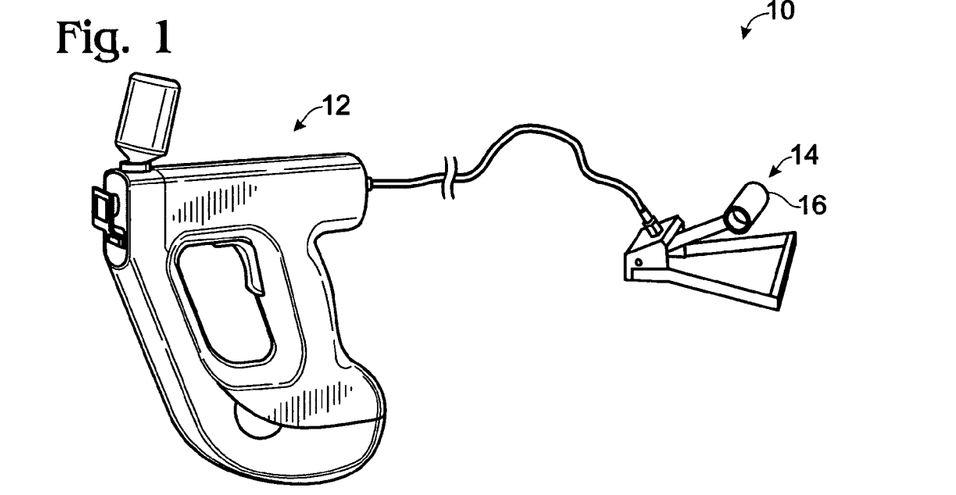
FIG. 1 is a perspective view of a needle-free injection system according to the present description.

Referring to FIG. 1, a needle-free injection system 10 according to the present description is depicted. As shown in FIG. 1, the system may include a handpiece 12 configured to deliver an injection to an injection site and an external actuating or arming mechanism 14, which may take the form of a foot pedal 16.

Figure 2:
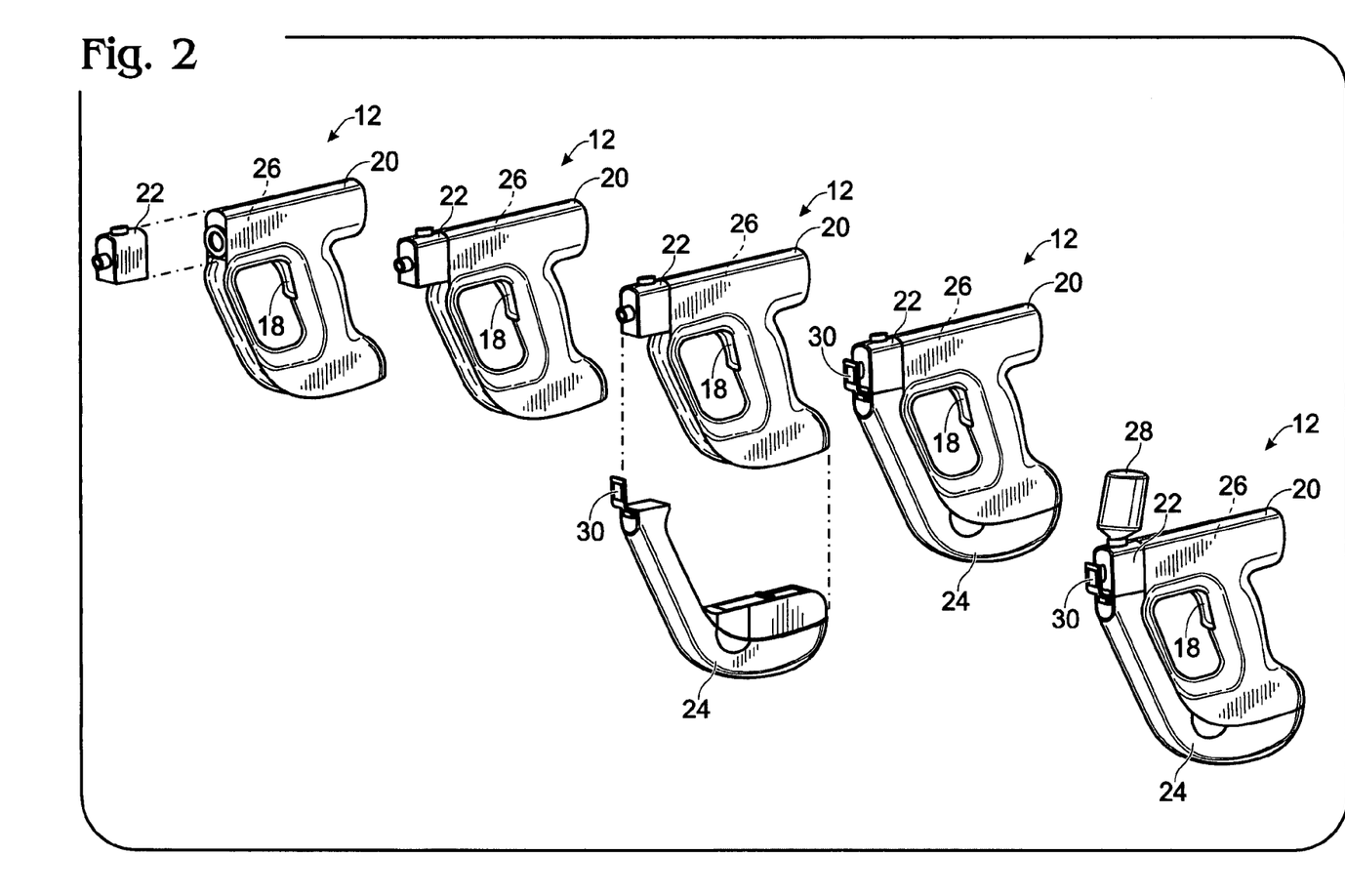
FIG. 2 is a perspective view of an embodiment of a handpiece showing various component parts in assembled and disassembled states.

Turning now to FIG. 2, handpiece 12 may include several component pieces: a main housing 20, a fluid path assembly 22, and a barrier dispenser cartridge 24. Main housing 20 may include an ejection or firing mechanism 26 (FIGS. 3–5), which may be activated via a trigger 18. The ejection/firing mechanism typically includes a plunger and/or other elements for providing pressure to deliver injections of fluid through fluid path assembly 22 to an injection site, as will be explained in detail below. Fluid path assembly 22 typically includes or is configured to receive a fluid chamber such as a vial or other container 28, which is adapted to hold one or more doses of injectable liquid. Barrier dispenser cartridge 24 is typically configured to dispense a barrier material 30 so as to reduce risk of cross contamination.

Figure 3:
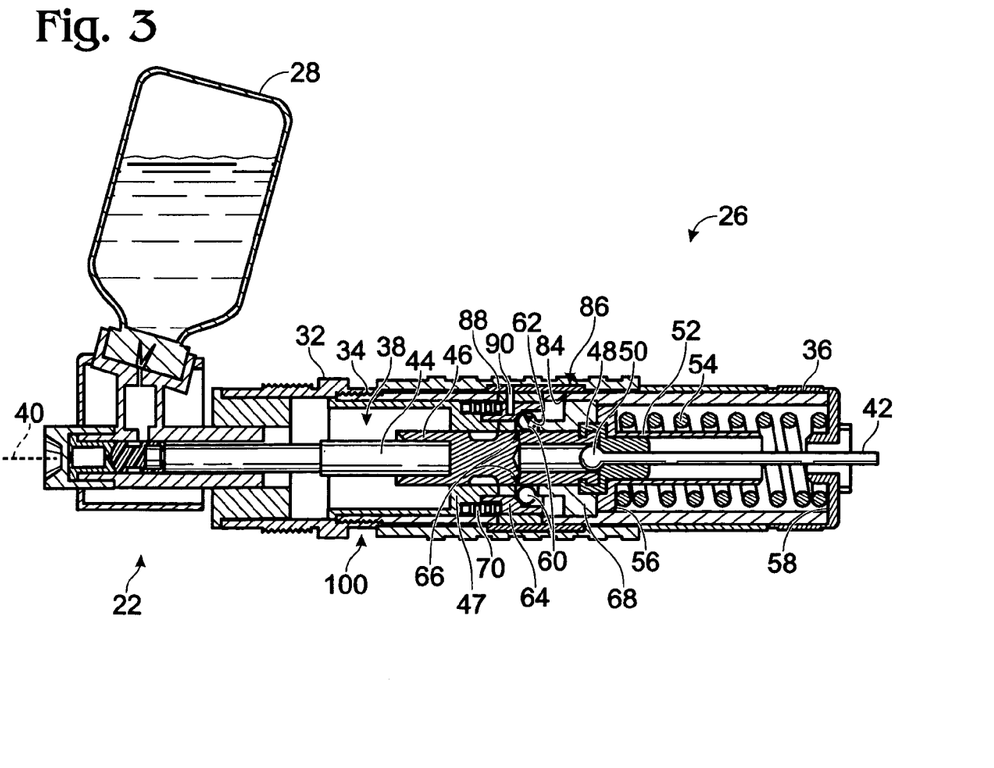
FIG. 3 is a cross-sectional view of a fluid path assembly connected to an ejection mechanism, showing the ejection mechanism in a relaxed state.
Figure 4:
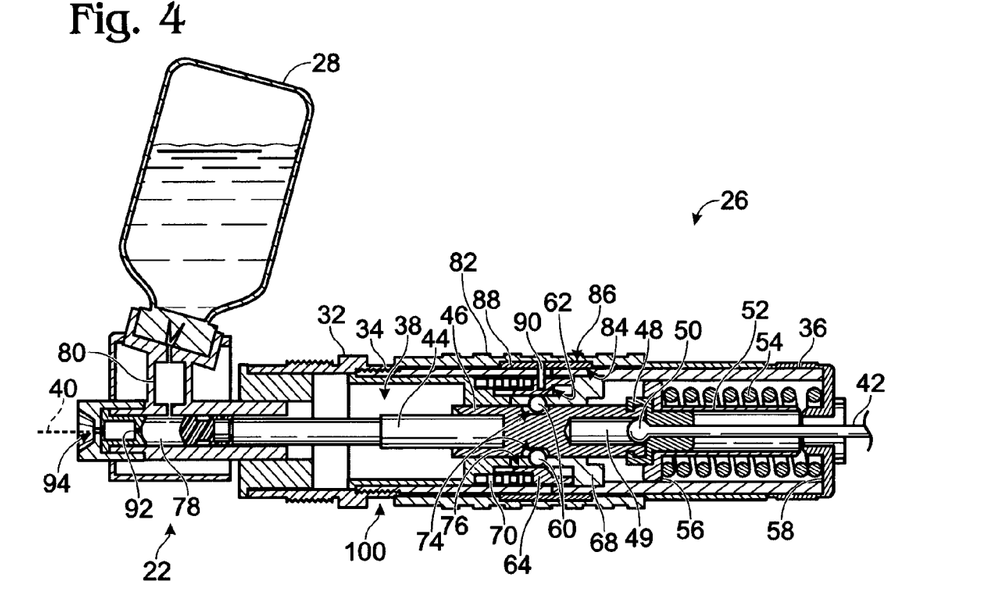
FIG. 4 is a cross-sectional view of the fluid path assembly and ejection mechanism of FIG. 3, shown in an armed state.
Figure 5:
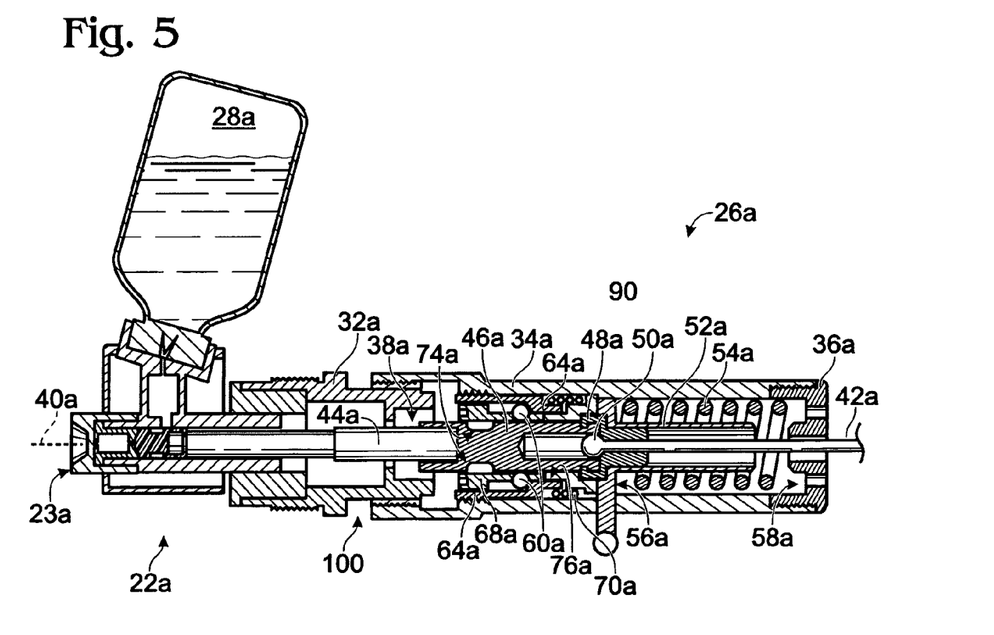
FIG. 5 is a cross-sectional view of a fluid path assembly connected to another embodiment of an ejection mechanism, showing the ejection mechanism in a relaxed state.

Referring now to FIGS. 3–5, the figures depict fluid path assembly 22 as connected to a forward end of ejection mechanism 26, which is typically held or secured within an upper portion of housing 20 (FIG. 2). Typically, fluid path assembly 22 is disposable, but may be subject to limited reuse. By limited reuse it is meant that the reusability of fluid path assembly 22 may be limited by time, number of injections given, etc. For example, fluid path assembly 22 may be configured such that once the first injection is given, that particular fluid path assembly can be used only for another 12 hours. Time of usage and number of injections delivered may be monitored via various sensors and accompanying circuitry, and/or through other suitable methods.

In the depicted example, ejection mechanism 26 includes a forward housing 32, a central housing 34, a rear housing 36 and a plunger assembly 38, which may be aligned as indicated along injection axis 40. Plunger assembly 38 may be configured to retract in a rearward direction (i.e., to the right in FIGS. 3–5) when cable 42 is pulled (e.g., when a user steps on foot pedal 16), and may include a plunger 44 and locking member 46 slidably held within guide 47. As shown, plunger assembly 38 may also include a capture member 48 (e.g., for holding an anchor 50 affixed to the end of cable 42) and rear member 52. Main spring 54 is positioned so as to urge against a lip portion 56 of rear member 52 and a rear portion 58 of rear housing 36. Spring 54 compresses as plunger assembly 38 is retracted toward the rear of ejection mechanism 26.

Turning specifically to the embodiment shown in FIGS. 3 and 4, when spring 54 is relaxed, i.e. before an injection is initiated or after an injection is completed (FIG. 3), balls 60 are seated between an inclined lip portion 62 of slide bushing 64 and notch 66 in locking sleeve 68. A spring 70 is provided between slide bushing 64 and retaining sleeve 72. Spring 70 is biased to urge slide bushing 64 rearwards, i.e. towards main spring 54. However, with balls 60 seated as shown, slide bushing 64 is trapped between spring 70 and balls 60 and cannot move.

As plunger assembly 38 is retracted, as shown in FIG. 4, a circumferential groove 74 provided on locking member 46 will eventually come into alignment with balls 60. At that point, spring 70 and an inclined lip portion 62 of slide bushing 64 cooperate to push the balls into groove 74. Slide bushing 64 is then permitted to move to a rearward position in which balls 60 are prevented from moving outward from groove 74 by an inward-facing surface 76 of the slide bushing. In this position, the interaction between balls 60 and groove 74 prevents the plunger assembly from moving forward, despite the force being exerted due to the compression of spring 54.

Retraction of plunger assembly 38 also causes a dose of injectable liquid to be drawn from container 28 into an injection cylinder 78 defined within fluid path assembly 22. Specifically, liquid is drawn through inlet 80 past a ball-type inlet check valve (not shown) configured to prevent backflow into container 28.

In the state just described—that is, with the plunger assembly retracted and a dose of liquid drawn into injection cylinder 78—the system is armed and ready to deliver an injection. Ejection mechanism 26 may then be fired by placing the forward end of fluid path assembly 22 against an injection site and operating trigger 18 (FIGS. 1 and 2), which acts to slide a trigger sleeve 82 forward relative to central housing 34. It should be noted, however, that a contamination barrier may be placed between the fluid path assembly and the injection site, as described above and in greater detail below.

A portion 84 of trigger sleeve 82 is threaded to a portion 86 of collar 88. Extending inward from collar 88 is one or more dowel pins 90. For example, a preferred embodiment may include three dowel pins spaced at 120° intervals around the inner circumference of collar 88. Each dowel pin extends through the central housing into slide bushing 64. As trigger sleeve 82 is moved forward, central housing 34 and slide bushing 64 are moved forward. As slide bushing 64 moves forward, a space is made available into which balls 60 may move in response to the sizable forward-directed force being exerted upon the plunger assembly by spring 54.

Spring 54 then decompresses, causing plunger assembly 38 to move forward rapidly and thereby expel liquid from injection cylinder 78 out and into the injection site. Specifically, fluid is forced through nozzle outlet 92, which may be sealed with a spring-biased ball-type check valve (not shown), and through nozzle outlet 94. As discussed above, a contamination barrier may be placed between the fluid path and injection site, in which case the fluid must penetrate the barrier before entering the injection site. A return spring (not shown), biased against forward movement of trigger sleeve 82 may be provided to return the trigger sleeve to the original pre-injection position.

In an alternative embodiment, depicted in FIG. 5, balls 60a are held in place via a locking sleeve 68a that is fixed relative to rear housing 36a. Spring 70a is provided between a rear lip 65a of slide bushing 64a and locking sleeve 68a, thereby urging slide bushing 64a forward. As plunger assembly 38a is retracted, a circumferential groove 74a provided on cable piston 46a will eventually come into alignment with balls 60a. Forward motion of slide bushing 64a is prevented by balls 60a, however, until groove 74a is aligned with the balls. At that point, spring 70a and an inclined lip portion 62a of the slide bushing cooperate to push the balls into groove 74a. Slide bushing 64a is then permitted to move to a forward position in which balls 60a are prevented from moving outward from groove 74a by inward-facing surface 76a of the retaining sleeve. In this position, the interaction between balls 60a and groove 74a prevents the plunger assembly from moving forward, despite the force being exerted due to the compression of spring 54a.

Once the plunger assembly is retracted and a dose of liquid is drawn into the injection cylinder, the system is armed and ready to deliver an injection. Ejection mechanism 26a may then be fired by pressing the forward end 23a of fluid path assembly 22a onto an injection site. As with the embodiment described above, a contamination barrier may be placed between the fluid path assembly and the injection site.

Pressing the fluid path assembly onto the injection site causes forward housing 32a to move rearward and thus push slide bushing 64a in a rearward direction. After a relatively small amount of rearward travel, the slide bushing moves into a position in which the balls are able to move outward into the recess in which they rested prior to arming of the device. Indeed, the balls are rapidly forced into this outward position due to the sizable forward-directed force being exerted upon the plunger assembly by spring 54a. As with the embodiment described above, spring 54a then decompresses, causing plunger assembly 38a to move forward rapidly and thereby expel liquid from the injection cylinder out and into the injection site.

Figure 6:
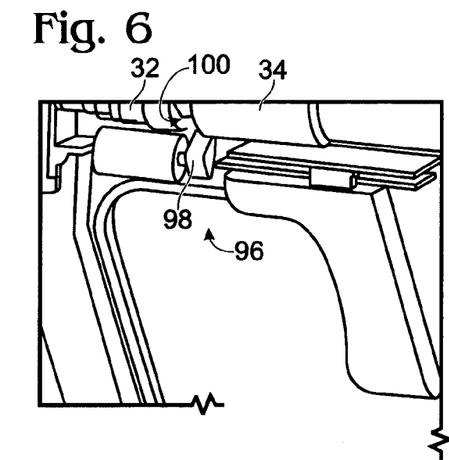
Figure 7:
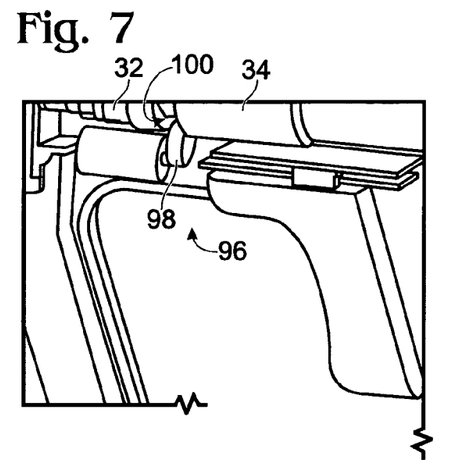

Optionally, a safety or like disabling mechanism may be provided, so that an injection cannot be delivered unless certain conditions are satisfied. An exemplary safety mechanism is shown in FIGS. 6 and 7. In the depicted example, actuating safety mechanism 96 actuates a motor that causes member 98 to be selectively moved out of a gap 100. Referring to the above exemplary embodiments, the gap is defined between housing components that are moved relative to each other in order to trigger the injection. For example, in the embodiment of FIGS. 3 and 4, gap 100 is defined between forward housing 32 and trigger sleeve 82. After the device is armed, trigger sleeve 82 must be moved forward relative to forward housing 32, thereby closing gap 100, in order to provide an injection. Accordingly, member 98 (FIG. 7) must be retracted to provide an injection, so that it does not obstruct the relative movement required to release the ejection mechanism from its armed state. In the example of FIG. 5, gap 100 is defined between forward housing 32a and central housing 34a. In either case, an injection cannot be provided unless the obstructing member 98 is removed via operation of trigger 102. It should be understood that in addition to selectively retracting member 98, trigger 102 may be mechanically coupled with the various housing members so as to provide the relative movement necessary to fire the device. Furthermore, it may be desirable to prevent retraction of member 98 unless certain other conditions are satisfied in addition to the pulling of trigger 102. For example, as will be explained in detail below, member 98 may be prevented from retracting unless certain conditions relating to sterilization and/or avoidance of cross-contamination are satisfied.

Figures 8, 9, 15:
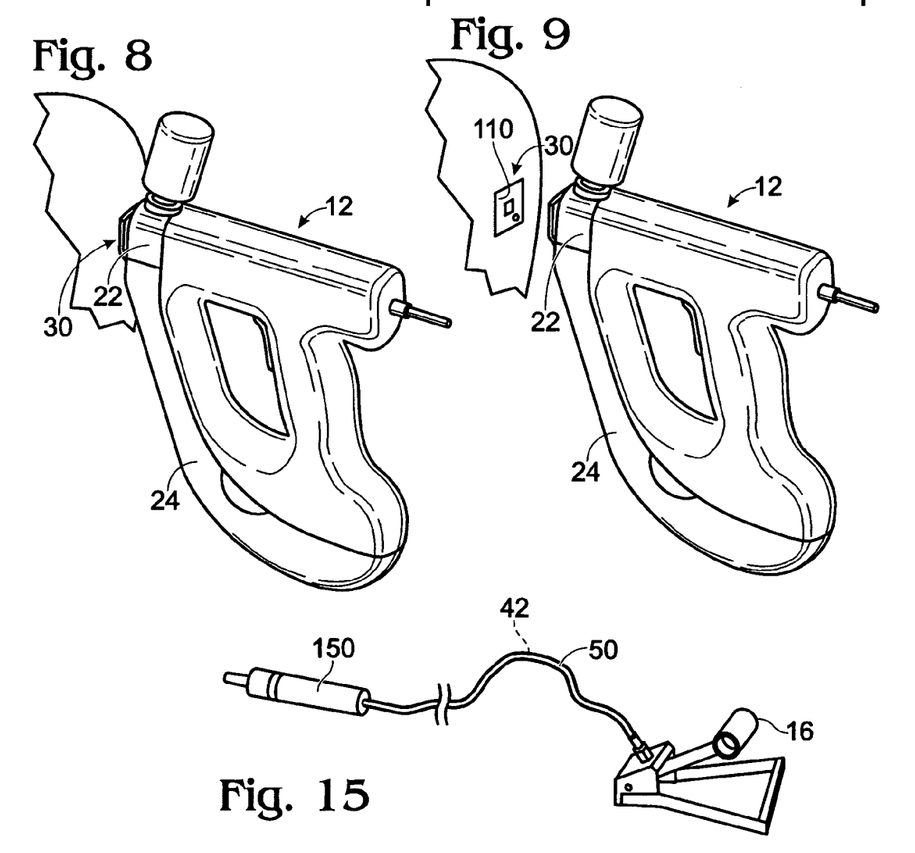
FIGS. 8 and 9 are elevation views depicting the needle-free injection system delivering an injection through a barrier material.
FIG. 15 is a perspective view of an embodiment of an external actuating mechanism.

Turning to FIGS. 8–14, attention will now be paid to an exemplary contamination barrier according to one embodiment of the present invention. As stated above, cartridge 24 may be configured to dispense a barrier material 30 so as to reduce risk of cross-contamination. In particular, cartridge 24 may be configured to provide, for each injection, a piece or section of barrier material (e.g., a patch) that is positioned between the injection site (e.g., a patient's skin) and the operative end of fluid path assembly 22 (FIGS. 8 and 9). The barrier material may be adapted to permit the injected liquid to penetrate through the barrier from the injection device into the injection site, while preventing the injected liquid from splashing back through the barrier toward the injection device. Typically, as will be explained below, it will be desirable that upon delivery of an injection, the section of barrier material used for that injection separate away from the needle-free injection device, and that such separation occur automatically without further action being taken by the operator of the device.

Figure 10:
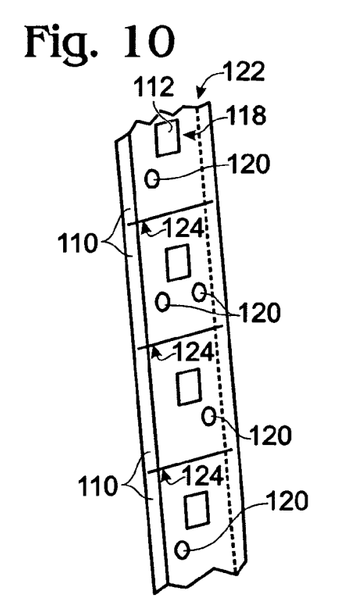
FIG. 10 depicts a strip of adhesive patches including barrier material.
Figure 11:
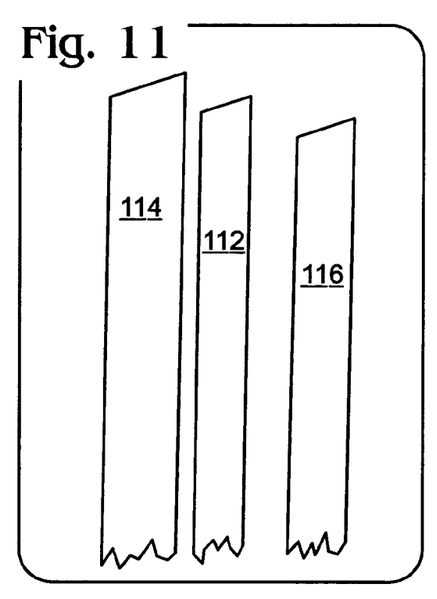
FIG. 11 depicts three component layers of the strip of FIG. 10.

In certain embodiments, the contamination barrier may take the form of a single-use adhesive patch 110 that is positioned over the nozzle outlet and that removably adheres to the injection site during an injection. As shown in FIGS. 10 and 11, each adhesive patch may be formed from three layers of material. For example, a layer of barrier material 112 may be sandwiched between a first external layer 114 and a second external layer 116. Each of the external layers will typically provide a window 118 through which the barrier material is accessible. Typically, the first external layer is coated with an adhesive that will removably adhere the patch to an area on the injection recipient such that the intended injection site is covered only by the barrier material. The second external layer may include detectable markings or other indicia 120, which may, for example be detectable by an optical reader or other sensor as will be described in greater detail below. The resilient material may, for example, have a thickness of less than 0.008 inches. Of course it will be appreciated that the adhesive patch may be formed using more or fewer layers of material. The layer or layers that form the adhesive patches may be formed into a strip or elongate tape 122, in which the patches are aligned edge to edge. The strip may be pre-scored, as shown at 124 to facilitate separation into individual patches.

Figure 12:
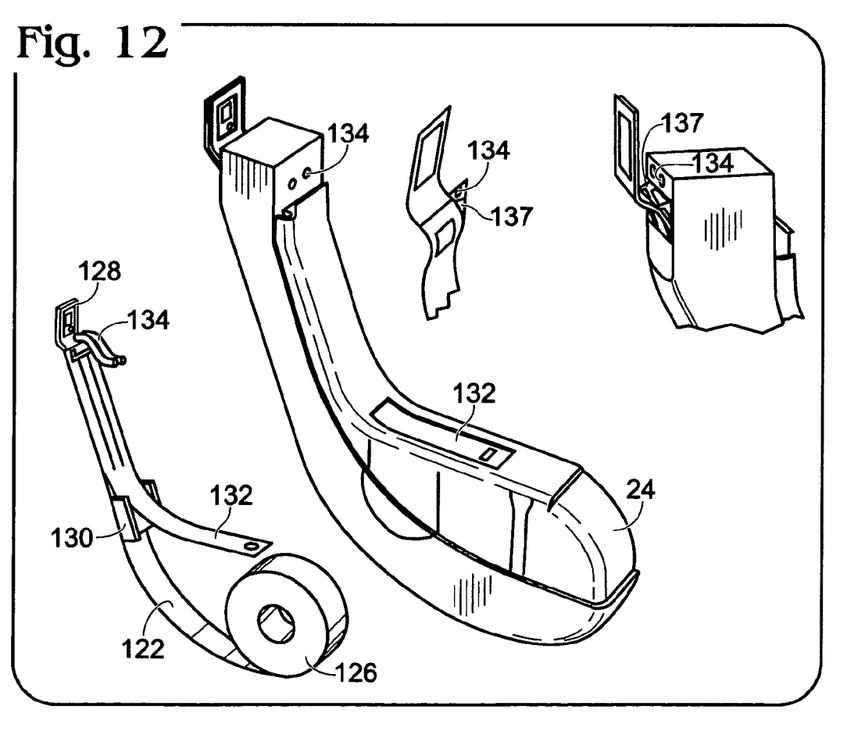
FIG. 12 depicts a barrier dispensing cartridge.

An exemplary removable cartridge 24 is shown in FIG. 12. Cartridge 24 may include a spool or reel 126, a positioner 128, a guide 130, an advancement separation mechanism 132, and optical sensors 134. As shown, strip 122 may be wound around spool 126 and then threaded through guide 130 such that a new patch is presented or advanced into position for each injection.

Figure 13:
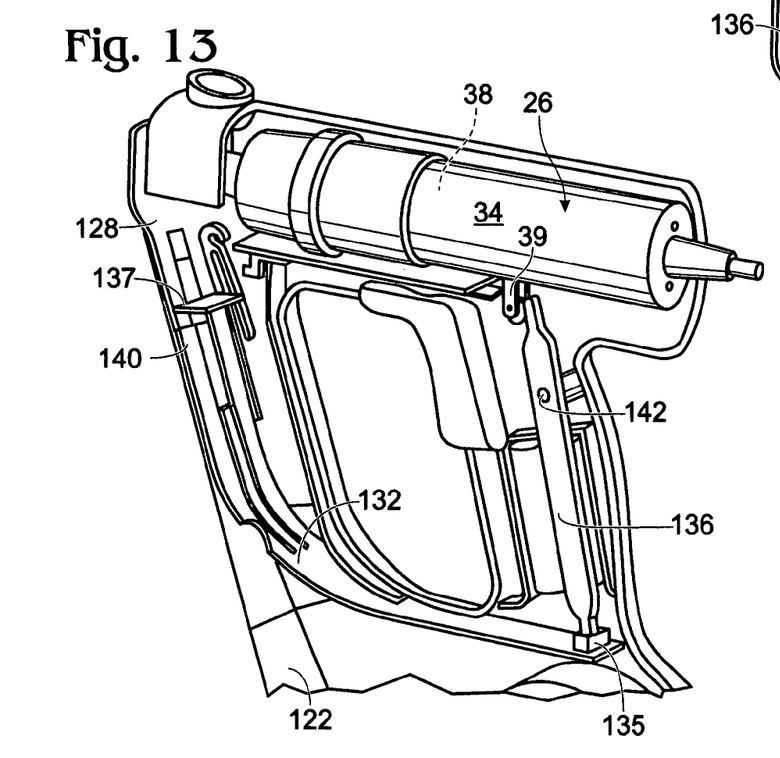
FIGS. 13 and 14 are partial sectional views of the handpiece showing an adhesive strip separation mechanism.
Figure 14:
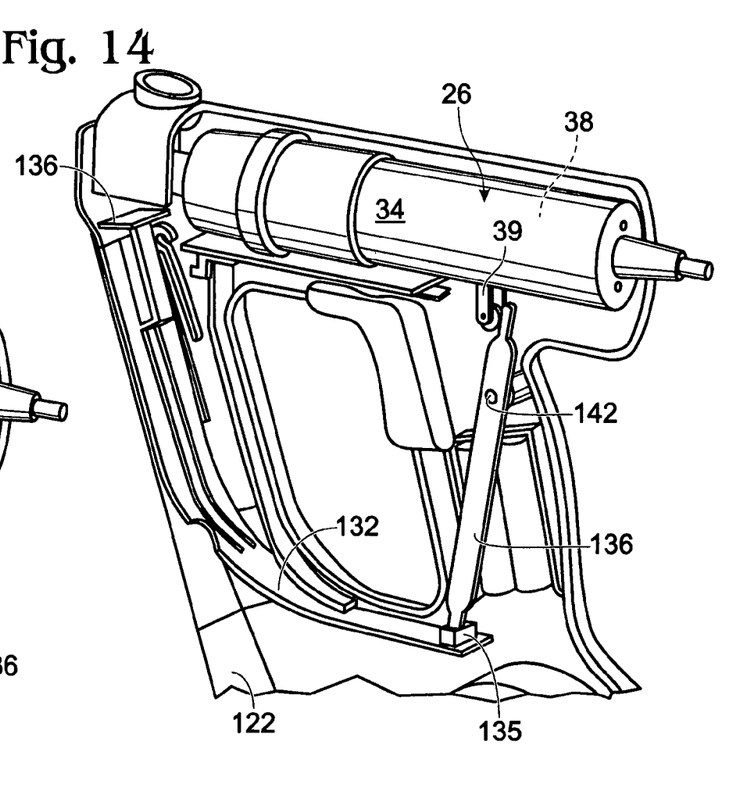

The injection device may be configured so that a new, unused patch is positioned in positioner 128 as the device is being armed. Typically, this is achieved through operative engagement of the firing/ejection mechanism with the supply of barrier material, so that arming of the device advances a new section of barrier material into position over the nozzle outlet. For example, as shown in FIGS. 13 and 14, it can be seen that an advancement or patch feed mechanism 132 is connected at end 135 to pivot arm 136, which is, in turn, operatively coupled with plunger assembly 38 of firing mechanism 26. End 140 of advancement mechanism 132 is slidably received by positioner 128. As shown, pivot arm 136 is attached to main housing 20 at pivot point 142 such that rearward movement of central housing 34, as would take place during an injection, translates into upward movement of advancement mechanism 132, and thus an advancement of tape 122 within barrier dispenser cartridge 24. This upward movement of advancement mechanism 132 positions cutter 137 such that cutter 137 is able to separate the advanced patch from the rest of the tape strip along scoreline 124.

Because the patches are used to provide a splashback barrier to prevent cross-contamination between injection recipients, it may be desirable to ensure that the patches cannot be reused and/or to ensure that a new patch is advanced into place for each injection. As stated above, each patch may include detectable markings or other detectable indicia 120 (FIG. 10). These markings may be detected by optical sensors 134, which may be in electronic communication with a processor (not shown). The markings on the patches may follow a predetermined sequence, so that as the markings are read by the sensor, the processor may ensure that the proper sequence is followed. When such indicia are employed, the injection device may be configured to prevent firing upon detection of an interruption in the predetermined sequence, as would occur in the event that a fresh patch was not advanced into place (e.g., through jamming or other malfunction of the advancement mechanism). Disabling of the firing mechanism may be achieved through use of the trigger and obstructing member described above with reference to FIGS. 6 and 7.

For example, the markings could be reflective dots arranged in a repeating pattern. A first patch might have a single dot on the lower left-hand corner, a second patch might have a dot on the lower left-hand corner and a dot on the lower right-hand corner, and a third patch might have a single dot on the lower right-hand corner, this pattern could then be repeated along the entire tape strip.

If the optical sensors detect a marking that is out of order or otherwise unexpected, i.e. two patches in a row having single dots on the lower left-hand corner, the device may be configured to prevent an injection from taking place and/or alert the user, for example, with a visible, audible, or other signal. Of course, it will be appreciated that different types of markings or sensible indicia may be employed, such as individual serial numbers, barcodes, etc.

Returning to FIG. 1, the external actuating mechanism 30 (e.g., the depicted foot pedal assembly) may be configured to facilitate arming of the injection system. For example, as explained in detail above, the depicted exemplary device may be configured to employ spring force in delivering injections. Accordingly, actuating mechanism 30 may be implemented with a foot pedal 16 that retracts a cable (cable 42 and **42*a* in FIGS. 3–5) when depressed, so as to arm (e.g., compress) spring 54 within handpiece 20. FIG. 15 depicts another view of foot pedal 16, cable 42 within cable housing 51, and a portion of the ejection mechanism which may be housed within handpiece 12**.

The exemplary depicted configuration allows the actuating mechanism to compress the main spring with a single motion, i.e. by depressing the foot pedal once. As described above, the device may be configured such that compression of the spring results in simultaneous transfer of a dose of injection fluid into the fluid path assembly. Thus, the user need only depress the foot pedal a single time to fully arm the device between injections.

It will in some cases be desirable to operatively couple certain components to plunger assembly 38 so that such components do not create drag on the plunger assembly as it advances forward during firing. For example, locking member 46 may be provided with a cable anchor cavity 49, into which anchor 50 may advance as foot pedal 16 is released just prior to firing of the device. Release of the pedal causes the cable to advance forward so that anchor 50 is received within a forward end of cavity 49. Accordingly, when the device is fired, the forward action of plunger assembly 38 will not be hindered by cable 42. Similarly, pivot arm is not fixedly secured to plunger assembly 38. Instead, the pivot arm bears against but is not attached to a pin 39 that extends outward from the plunger assembly. Accordingly, rearward movement of plunger assembly 38 (e.g., during arming of the device) causes the pivot arm to move and thus advance tape 122. However, forward movement of plunger assembly 38 does not drag the upper end of pivot arm 136 forward, because the pivot arm is not fixedly secured to pin 39. Accordingly, pivot arm 136 does not drag upon the plunger assembly during firing. Instead, pivot point 142 is biased with a spring so as to bring the upper end of pivot arm 136 forward upon firing of the device.

While various alternative embodiments and arrangements of a needle-free injection system and method have been shown and described above, it will be appreciated that numerous other embodiments, arrangements, and modifications are possible and are within the scope of the invention. The foregoing description should be understood to include all novel and non-obvious combinations of elements described herein, and claims may be presented in this or a later application to any novel and non-obvious combination of these elements. The foregoing embodiments are illustrative, and no single feature or element is essential to all possible combinations that may be claimed in this or a later application.

The invention claimed is:

1. A needle-free injection device, comprising:
a nozzle including an outlet;
a fluid chamber in fluid communication with the outlet and configured to store fluid to be injected, where the needle-free injection device is configured to deliver multiple injections of fluid from the fluid chamber out through the outlet of the nozzle and into one or more injection sites;
a plurality of contamination barrier patches, each contamination barrier patch being adapted to allow fluid ejected at sufficient pressure from the outlet to penetrate out through the contamination barrier patch while substantially preventing fluid splashback toward the needle-free injection device, where the contamination barrier patches are provided as an elongate tape in which the contamination barrier patches are arranged edge to edge
the needle-free injection device being configured so that one contamination barrier patch is provided for each injection, and for each injection, the contamination barrier patch separates away from the needle-free injection device after delivery of the injection; and
a patch feed mechanism configured to enable positioning of one of the contamination barrier patches over the outlet of the nozzle for each injection to be delivered, such that when the outlet is placed near an injection site, the contamination barrier patch is positioned between the outlet and the injection site.

2. The device of claim 1, where the patch feed mechanism includes a supply reel on which the elongate tape of contamination barrier patches is stored.

3. The device of claim 2, further comprising a firing mechanism configured to be repeatedly armed and fired, where firing the firing mechanism causes fluid within the fluid chamber to be forcibly ejected from the fluid chamber and out through the outlet, and where the firing mechanism is operatively engaged with the supply reel such that arming of the firing mechanism causes the supply reel to rotate and thereby advance a fresh one of the contamination barrier patches into position over the outlet of the nozzle.

4. The device of claim 1, where on the elongate tape, successive contamination barrier patches are provided with a predetermined sequence of indicia, and where the needle-free injection device further comprises a disabling mechanism responsive to the indicia and configured to prevent delivery of an injection upon detection of an interruption in the predetermined sequence.

5. A needle-free injection device, comprising:
a nozzle including an outlet;
a fluid chamber in fluid communication with the outlet and configured to store fluid to be injected, where the needle-free injection device is configured to deliver multiple injections of fluid from the fluid chamber out through the outlet of the nozzle and into one or more injection sites;
a plurality of contamination barrier patches, each contamination barrier patch being adapted to allow fluid ejected at sufficient pressure from the outlet to penetrate out through the contamination barrier patch while substantially preventing fluid splashback toward the needle-free injection device,
where the needle-free injection device is configured so that one contamination barrier patch is provided for each injection, and where the needle-free injection device is configured so that for each injection, the contamination barrier patch separates away from the needle-free injection device after delivery of the injection, and
a firing mechanism configured to be repeatedly armed and fired, where firing the firing mechanism causes fluid within the fluid chamber to be forcibly ejected from the fluid chamber and out through the outlet, where the firing mechanism is operatively engaged with the plurality of contamination baffler patches such that arming of the firing mechanism causes a fresh one of the contamination barrier patches to be advanced into position over the outlet of the nozzle.

6. A needle-free injection device, comprising:
a nozzle including an outlet:
a fluid chamber in fluid communication with the outlet and configured to store fluid to be injected, where the needle-free injection device is configured to deliver multiple injections of fluid from the fluid chamber out through the outlet of the nozzle and into one or more injection sites;
a plurality of contamination barrier patches, each contamination barrier patch being adapted to allow fluid ejected at sufficient pressure from the outlet to penetrate out through the contamination barrier patch while substantially preventing fluid splashback toward the needle-free injection device,
where the needle-free injection device is configured so that one contamination barrier patch is provided for each injection, and where the needle-free injection device is configured so that for each injection, the contamination barrier patch separates away from the needle-free injection device after delivery of the injection, and remains at the injection site upon withdrawal of the needle-free injection device from the injection site.

7. The device of claim 6, where each contamination barrier patch is provided with adhesive on a side facing the injection site to facilitate retention of the contamination barrier patch at the injection site after delivery of the injection.

8. A needle-free injection device, comprising:
a nozzle including an outlet;
a fluid chamber in fluid communication with the outlet and configured to store fluid to be injected;
a firing mechanism configured to be repeatedly armed and fired, where firing the firing mechanism causes fluid within the fluid chamber to be forcibly ejected from the fluid chamber and out through the outlet, and where the firing mechanism includes a spring configured to provide force to aid in forcibly ejecting fluid form the fluid chamber;

an arming mechanism including a foot pedal assembly and a cable operatively coupled between the foot pedal assembly and the spring of the firing mechanism, such that, upon operation of the foot pedal assembly by a user, the cable is pulled so as to compress the spring and thereby arm the firing mechanism; and a supply of contamination barrier patches, each contamination barrier patch being adapted to allow fluid ejected at sufficient pressure from the outlet to penetrate out through the contamination barrier patch while substantially preventing fluid splashback toward the needle-free injection device, and where the firing mechanism is operatively engaged with the supply of contamination barrier patches such that arming of the firing mechanism causes a fresh unused contamination barrier patch to be positioned over the outlet of the nozzle.

9. The device of claim 8, further comprising a disabling mechanism configured to prevent delivery of an injection upon detection by the disabling mechanism that a fresh contamination barrier patch has not been positioned over the outlet of the nozzle for the injection.

10. A needle-free injection device, comprising:
a nozzle including an outlet;
a fluid chamber in fluid communication with the outlet and configured to store fluid to be injected;
a firing mechanism configured to be repeatedly armed and fired, where firing the firing mechanism causes fluid within the fluid chamber to be forcibly ejected from the fluid chamber and out through the outlet;
a quantity of disposable barrier material adapted to prevent contamination, the barrier material being adapted to allow fluid ejected at sufficient pressure from the outlet to penetrate out through the barrier material while substantially preventing fluid splashback, and where the barrier material is provided as a plurality of single-use sections; and
a disabling mechanism adapted to prevent the firing mechanism from being fired unless the disabling mechanism detects that a fresh unused section of barrier material has been positioned over the outlet of the nozzle for the upcoming injection.

11. The device of claim 10, where the firing mechanism includes a spring that is compressed and retained in a compressed state upon arming of the firing mechanism, and that is released in order to fire the firing mechanism.

12. The device of claim 11, where the needle-free injection device is configured so that the firing mechanism and spring are released upon pressing of a front portion of the needle-free injection device onto an injection site.

13. The device of claim 12, where the needle-free injection device is configured so that the pressing of the needle-free injection device onto the injection site causes a relative movement between component parts of the needle-free injection device, said relative movement triggering release of said spring from the compressed state to thereby permit decompression of the spring and firing of the firing mechanism.

14. The device of claim 10, where the single-use sections are contamination barrier patches, one such contamination barrier patch being provided for each injection delivered to an injection site, and where the needle-free injection device is configured so that for each injection, the contamination barrier patch used for such injection separates away from the needle-free injection device and remains at the injection site upon withdrawal of the needle-free injection device from the injection site.

15. The device of claim 10, where the single-use sections are contamination barrier patches, one such contamination barrier patch being provided for each injection, and where the firing mechanism is operative engaged with the quantity of disposable barrier material so that a fresh contamination barrier patch is advanced into position over the outlet of the nozzle upon arming of the firing mechanism.

16. The device of claim 10, where the single-use sections are provided as an elongate tape of contamination barrier patches marked with a predetermined sequence of indicia, and where the disabling mechanism is configured to prevent the firing mechanism from being fired upon detection of an interruption in the predetermined sequence.

17. A needle-free injection device, comprising:
a nozzle including an outlet;
a fluid chamber in fluid communication with the outlet and configured to store fluid to be injected;
a firing mechanism configured to be repeatedly armed and fired, where firing the firing mechanism causes fluid within the fluid chamber to be forcibly ejected from the fluid chamber and out through the outlet, the firing mechanism including a spring that is compressed and retained in a compressed state upon arming of the firing mechanism, and that is released in order to fire the firing mechanism, and the firing mechanism and spring are released upon pressing of a front portion of the needle-free injection device onto an injection site;
a disabling mechanism configured to prevent firing of the firing mechanism if one or more components of the needle-free injection device have been used beyond a predetermined use threshold, where the disabling mechanism includes an obstructing member configured to block said relative movement between component parts of the needle-free injection device and thereby prevents firing of the firing mechanism unless the disabling mechanism detects that said predetermined use threshold has not been exceeded and that an unused contamination barrier has been positioned over the outlet of the nozzle;
where the needle-free injection device is configured so that the pressing of the needle-free injection device onto the injection site causes a relative movement between component parts of the needle-free injection device, said relative movement triggering release of said spring from the compressed state to thereby permit decompression of the spring and firing of the firing mechanism.

18. A needle-free injection device comprising:
a nozzle including an outlet;
a fluid chamber in fluid communication with the outlet and configured to store a dose of fluid;
a firing mechanism configured to be repeatedly armed and fired, where firing the firing mechanism causes fluid within the fluid chamber to be forcibly ejected from the fluid chamber and out through the outlet;
a quantity of disposable barrier material supported near the nozzle, the barrier material being adapted to allow fluid ejected at sufficient pressure from the outlet to penetrate out through the barrier material while substantially preventing fluid splashback; and
an advancement mechanism operatively engaged with the firing mechanism such that arming of the firing mechanism causes the advancement mechanism to advance an unused section of the disposable barrier material into a position in which the unused section of barrier material covers the outlet of the nozzle.

19. The device of claim 18, where the firing mechanism includes a spring that is compressed to arm the firing mechanism, and where subsequent decompression of the spring causes fluid within the fluid chamber to be forcibly ejected from the fluid chamber and out through the outlet.

20. The device of claim 19, further comprising a lever and a cable operatively coupled with the spring, where the spring, cable and lever are configured so that operation of the lever pulls the cable to thereby compress the spring and arm the firing mechanism.

21. The device of claim 20, further comprising a foot pedal connected to the lever, so that a user can operate the lever and thereby arm the firing mechanism by stepping on the foot pedal.

22. The device of claim 18, where the firing mechanism is configured so that, after the firing mechanism has been armed, the firing mechanism is fired by pressing the needle-free injection device onto an injection site into which is an injection is to be provided.

23. The device of claim 22, where the needle-free injection device includes a disabling mechanism that prevents firing of the firing mechanism if one or more predetermined conditions is met, in which case the disabling mechanism prevents firing even if the needle-free injection device is pressed onto the injection site.

24. The device of claim 23, where the disabling mechanism is configured to determine whether one or more components of the needle-free injection device has been in use for longer than a predetermined threshold period of time, and where the disabling mechanism prevents firing of the firing mechanism if such predetermined threshold period of time has been exceeded.

25. The device of claim 23, where the disabling mechanism includes a sensor configured to sense indicia provided on the barrier material, and where the disabling mechanism prevents firing of the firing mechanism if such sensing indicates the a new section of barrier material has not been advanced into place for the upcoming injection.

26. The device of claim 18, where the quantity of disposable barrier material is provided on a reel, and where the reel is rotated to advance the unused section of barrier material into position upon arming of the firing mechanism.

27. The device of claim 26, where the barrier material has adhesive on a side of the barrier material facing away from the outlet.

28. The device of claim 26, where the barrier material is situated on the reel as a plurality of patches aligned edge to edge as an elongate tape, and where indicia is provided on successive patches in a predetermined indicia sequence, the needle-free injection device further comprising a sensor configured to detect interruptions in the predetermined indicia sequence.

29. The device of claim 26, where the barrier material is situated on the reel as a plurality of patches aligned edge to edge as an elongate tape, and where the needle-free injection device further includes a cutter adapted to cut the unused section of barrier material away from the tape as the firing mechanism is armed.

30. A needle-free injection device, comprising:
a nozzle including an outlet;
a fluid chamber in fluid communication with the outlet and configured to store a dose of fluid;
a firing mechanism configured to be repeatedly armed and fired, where firing the firing mechanism causes fluid within the fluid chamber to be forcibly ejected from the fluid chamber and out through the outlet, the firing mechanism being operable upon pressing of a front portion of the needle-free injection device onto an injection site so as to produce a relative movement between component parts of the needle-free injection device, said relative movement triggering a release mechanism which releases the firing mechanism from an armed state, thereby permitting firing of the firing mechanism; and
a disabling mechanism including an obstructing member configured to block said relative movement between component parts of the needle-free injection device and thereby prevent firing of the firing mechanism unless the disabling mechanism detects that an unused contamination barrier has been positioned over the outlet of the nozzle.

* * * * *